United States Patent
Quinn et al.

(10) Patent No.: US 6,943,887 B2
(45) Date of Patent: Sep. 13, 2005

(54) SURFACE PLASMON RESONANCE SENSOR HAVING REAL-TIME REFERENCING

(75) Inventors: John G. Quinn, Dallas, TX (US); Dwight U. Bartholomew, Dallas, TX (US); Richard A. Carr, Rowlett, TX (US)

(73) Assignee: Texas Instruments Incorporated, Dallas, TX (US)

(*) Notice: Subject to any disclaimer, the term of this patent is extended or adjusted under 35 U.S.C. 154(b) by 244 days.

(21) Appl. No.: 10/300,978

(22) Filed: Nov. 21, 2002

(65) Prior Publication Data

US 2003/0103208 A1 Jun. 5, 2003

Related U.S. Application Data

(60) Provisional application No. 60/336,565, filed on Dec. 4, 2001.

(51) Int. Cl.⁷ .............................................. G01N 27/17
(52) U.S. Cl. ....................................... 356/445; 356/369
(58) Field of Search ................................ 256/445, 446, 256/369

(56) References Cited

U.S. PATENT DOCUMENTS

| | | | | |
|---|---|---|---|---|
| 4,688,900 A | | 8/1987 | Doane et al. | 350/347 |
| 5,313,264 A | * | 5/1994 | Ivarsson et al. | 356/445 |
| 5,898,503 A | * | 4/1999 | Keller et al. | 356/445 |
| 5,912,456 A | | 6/1999 | Melendez et al. | 250/216 |
| 5,917,608 A | * | 6/1999 | Naya et al. | 356/445 |
| 5,943,129 A | * | 8/1999 | Hoyt et al. | 356/318 |
| 6,111,652 A | | 8/2000 | Melendez et al. | 356/445 |
| 6,183,696 B1 | * | 2/2001 | Elkind et al. | 356/445 |
| 6,424,418 B2 | * | 7/2002 | Kawabata et al. | 356/445 |
| 6,798,521 B2 | * | 9/2004 | Elkind et al. | 356/445 |
| 2003/0030817 A1 | * | 2/2003 | Lee et al. | 356/491 |

OTHER PUBLICATIONS

Reference–compensated Biosensing Using a Dual– Channel Surface Plasmon Resonance Sensor System Based on a Planar Lightpipe Configuration, Nenninger et al, University of Washington, pp 38–45.
Surface Plasmon Resonance Sensors: Review, Homola et al, University of Washington, pp 3–15.

* cited by examiner

*Primary Examiner*—Zandra V. Smith
*Assistant Examiner*—Juan D. Valentin, II
(74) *Attorney, Agent, or Firm*—William B. Kempler; W. James Brady, III; Frederick J. Telecky, Jr.

(57) ABSTRACT

A disposable, portable, miniature surface plasmon resonance sensor (30) having real-time referencing capability in the presence of any interaction, without changing the sensing surface condition is disclosed herein. The sensor (30) includes an electromagnetic radiation source (32) which generates a beam of electromagnetic radiation (52) that passes through a liquid crystal switch that includes a polarizer, plates and liquid crystal material sandwiched between the plates. The liquid crystal switch is disposed between the source (32) and an array of detectors (48). The liquid crystal switch has the ability to switch between a first and a second state of polarized radiation such that it provides the transverse magnetic component of the electromagnetic radiation for detection of SPR on a target element and, in the alternative, provides the transverse electric component of the electromagnetic radiation to determine a reference signal for the sensor (30). The polarized radiation is directed toward a layer (44) of a conductive material capable of sustaining surface plasmon resonance and reflected off layer (44) towards an array of electromagnetic radiation detectors (48) to make a determination of a property of the targeted element adjacent to layer (44) and produce an output signal in response to the received reflected electromagnetic radiation (52) indicative of the presence of, or representative of the concentration or a concentration range of, the targeted element.

12 Claims, 2 Drawing Sheets

SURFACE PLASMON RESONANCE SENSOR HAVING REAL-TIME REFERENCING

This application claims priority under 35 USC 119(e)(1) of provisional application No. 60/336,565 filed Dec. 4, 2001.

FIELD OF THE INVENTION

The present invention relates to optoelectric sensors, and, more particularly, to a surface plasmon resonance sensor having a real-time referencing feature capable of detecting interactions in real-time.

BACKGROUND OF THE INVENTION

Surface plasmon resonance is an optical phenomenon that results from wave vector matching between electromagnetic radiation undergoing total internal reflection from a thin SPR conductive metal surface and free electrons present at the thin SPR conductive metal surface. Sensors based upon SPR have been applied in a variety of applications in the fields of chemical, biochemical, biological or biomedical analysis. One such system, manufactured by Texas Instruments Incorporated™, is a low-cost, portable electronic sensor platform that determines the refractive index of a medium in contact with a thin conductive metal sensing surface as in described in U.S. Pat. No. 5,912,456, which is incorporated by reference herein. The sensitivity of this platform is confined to within approximately 200 nm of the SPR active surface which is ideal for a wide variety of chemical, biochemical and biomedical analysis applications. The design of the sensor facilitates large-scale production of low cost, disposable sensors. In a biosensor application, the absorption of biomolecules on the SPR active surface increases the refractive index which is monitored in real time by an electronic system supporting the optoelectric components of the sensor. The resulting interaction curve of refractive index change versus time, represents the binding profile of the biomolecule to the surface.

Specifically, an SPR sensor includes an electromagnetic radiation source, an optical aperture, a polarizer and detector array, all of which may be encapsulated in an optical medium, such as glass or transparent plastics, shaped to accommodate an optical path that supports SPR. Electromagnetic radiation from the source emerges from the aperture and is polarized to ensure that the transverse magnetic (TM) polarized component is retained while the transverse electric (TE) polarized component is eliminated. The TE polarized component is incapable of generating a resonance and is eliminated in order to reduce the fraction of non-interacting light reaching the detector array. The TM polarized light beam undergoes total internal reflection from the thin SPR conductive metal surface and reflects off of a mirror, which directs the reflected light onto the detector array. Resonance occurs when the wave vector of the incident TM polarized radiation matches the surface plasmon mode of the thin SPR conductive metal surface thus generating a charge density wave that adsorbs radiation at particular incident angles. The angular position of the resulting reflectance minimum is dependent upon the refractive index at the sensing surface and is detected by the detector array. The measurable range of the refractive index dependent resonance can be adjusted within certain theoretical limits by varying the range of incident angles employed. In addition, if an encapsulating optical medium is used, varying the refractive index of the encapsulating optical medium will adjust the measurable range of the refractive index dependent resonance.

Optical defects and temperature gradients cause time dependent interference in systems that use surface plasmon resonance. The time dependence of the interference severely reduces the effectiveness of the initial referencing and, hence, results in high noise levels. Conventionally, in an effort to reduce time dependent interference, a reference signal is obtained while the dielectric conditions adjacent to the thin SPR conductive metal surface foster an environment where no resonance occurs. To date this has been performed by exposing the sensing surface to a medium having a refractive index outside the SPR range for that particular sensor configuration. The signal obtained during resonance, when the sensing surface is exposed to the sample of interest, is divided by the non-resonance signal to give the corrected SPR signal. For example, exposing the sensing surface to air which has a refractive index of '1', or to glycerol which has a refractive index of '1.42', is appropriate for obtaining a non-resonance signal reading in a sensor having a refractive index measuring range from '1.333' to '1.40'. This procedure is highly effective when the optical system is stable.

Problems, however, arise when fluctuations in temperature and mechanical stress exist that generate optical defects within the light path give rise to interference, due to light scattering effects, that are variable with time. Hence, the non-resonance signal must be updated continuously, denoting real-time referencing, in order to minimize these interferences. This is difficult to perform, since it is necessary to ensure that the sensing surface is continuously in contact with the sample of interest.

Thus, a need exists for a disposable, portable, miniature surface plasmon resonance sensor having the ability to take a reference at any time in the presence of any interaction, without changing the sensing surface condition. In addition, there exists a need for such a system that has the ability to reduce baseline noise, improving the quality of the system substantially. This sensor must maintain high sensitivity and detection of analytes and must be cost effective to manufacture.

SUMMARY OF THE INVENTION

To address the above-discussed deficiencies of optoelectric biosensors, the present invention teaches a surface plasmon resonance sensor having real-time referencing. The sensor includes an electromagnetic radiation source which generates a beam of electromagnetic radiation having a magnetic component and a transverse electric component. A shield having an aperture couples to receive the radiation to minimize the deviation of the direction of the transmitted radiation from the source. An optical housing made of material which is capable of transmitting radiation from the source includes a film of conductive material capable of sustaining surface plasmon resonance. The film is disposed on an external surface of the optical housing. The optical housing and the film being shaped and positioned so that radiation from the source is reflected by the film and detected by a sensor array that is sensitive to the reflected radiation. The sensor array is disposed closely adjacent the surface of the optical housing. A switch is disposed between the source and the sensor array that has the ability to switch to provide the transverse magnetic component and the transverse electric component of optical radiation such that only one component strikes the sensor.

In one embodiment, the switch may be implemented using a polarizer coupled adjacent to a liquid crystal cell that includes of a liquid crystal material coupled between a pair of plates. The liquid crystal material rotates the molecular direction of the transmitted polarized radiation by 90 degrees such that the switch provides the transverse electric component of the optical radiation. A pair of electrodes attach to the liquid crystal material such that when a voltage is applied across the pair of electrodes, the switch provides the transverse magnetic component of the optical radiation, canceling the effect of the liquid crystal material upon the polarized radiation.

Advantages of this design include but are not limited to a disposable, portable, miniature surface plasmon resonance sensor having real-time referencing capabilities in the presence of any interaction, without changing the sensing surface condition. In addition, this sensor has the ability to reduce baseline noise, improving the quality of the system substantially. This sensor maintains high sensitivity and detection of analytes and is cost effective to manufacture.

BRIEF DESCRIPTION OF THE DRAWINGS

For a more complete understanding of the present invention and the advantages thereof, reference is now made to the following description taken in conjunction with the accompanying drawing in which like reference numbers indicate like features and wherein.

DETAILED DESCRIPTION OF PREFERRED EMBODIMENTS

Figure 1:
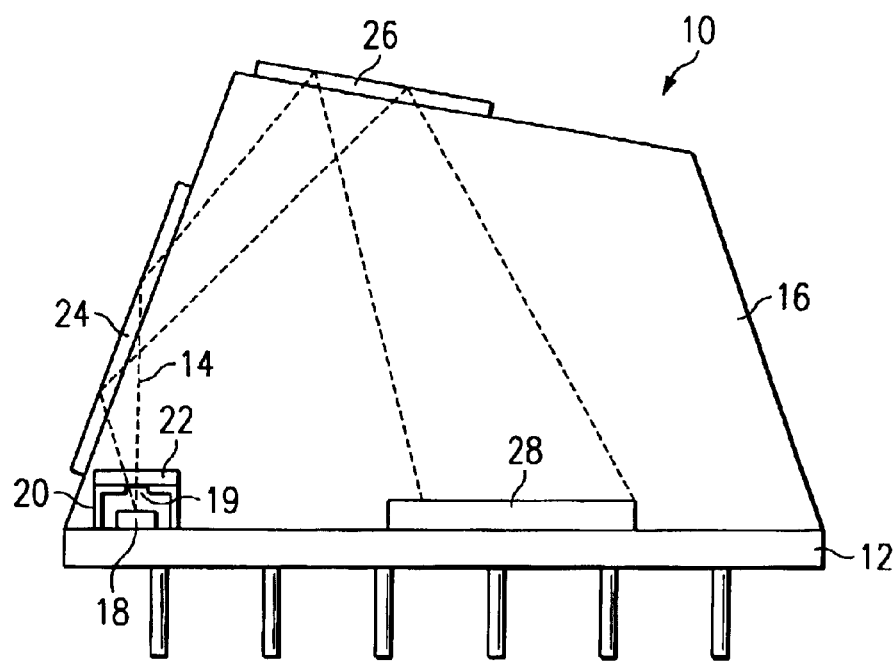
FIG. 1 illustrates a known optoelectric biosensor.

The present invention is best understood by comparison with the prior art. Hence, this detailed description begins with a discussion of known optoelectric biosensor shown in FIG. 1 as disclosed in U.S. Pat. No. 5,912,456 entitled "Integrally Formed Surface Plasmon Resonance Sensor". In this configuration, sensor 10 is constructed on a substrate 12. A radiation source 18, which may comprise a light emitting diode (LED), a laser diode or any other suitable source of radiation, is disposed internal to a housing 16 and is positioned to direct radiation (light rays) 14 in a direction toward a thin SPR conductive layer 24. Housing 16 is shaped to accommodate an optical path that supports surface plasmon resonance. Radiation source 18 is preferably located above substrate 12 although it can be disposed in substrate 12 itself. A physical shield 20 having an aperture 19 is disposed above radiation source 18 to create a guide through which light from source 18 passes.

Since the TE polarized component of radiation 14 is incapable of generating a resonance condition, it is necessary to eliminate this component and reduce the fraction of non-interacting light reaching detector array 28. Therefore, polarizing filter 22 is used to eliminate the TE polarized component of radiation 14 when it emerges from aperture 19. The TM polarized component of radiation 14 is retained and undergoes total internal reflection from layer 24 being directed onto a planar mirror 26, which directs the reflected light onto detector array 28.

Specifically, resonance occurs when the wave vector of the incident TM polarized light 14 matches the surface plasmon mode of layer 24 thus generating a charge density wave that results in the adsorption of light at particular incident angles. The angular position of the resulting reflectance minimum is dependent on the refractive index at the sensing surface portion of layer 24. As explained, when radiation 14 strikes thin conductive layer 24 at the interface of an insulator or housing 16, the intensity of reflection therefrom is a function of the angle of incidence of radiation 14 onto the layer 24 and the refractive index of the material in contact with the opposing side of the layer 24. Hence, by determining the angle at which minimum reflectance occurs, it is possible to determine the index of refraction of the material on the side opposite the side where radiation 14 reflects from. This angular position is detected by detector array 28. Detector array 28 may comprise a photodiode array. Given such case, each diode of detector array 28 produces a voltage proportional to the intensity of light striking its surface. The optical system including sensor 10 collects these intensity readings for each resonance signal and divides these signals by the data corresponding to a non-resonance signal or a reference signal to give a final corrected SPR signal.

Housing 16 is made of a material which is transparent or substantially transparent to the light from the light source 18. In particular, an epoxy marketed under the trademark Epocast® 2013 Parts A/B by Furane Products Company has been found useful especially for radiation sources in the infrared range. Other usable materials include Emerson & Cumming, Stycast 1269A Parts A/B, Tracon Trabond F114, Dexter Hysol OS1000, Norland 61 and 63, Dexter Hysol MG18 or Nitto 8510-1100.

Polarizer 22 does not need to be located closely adjacent the aperture 20 but may be disposed at any point along the path of radiation 14 between the source 18 and the detector array 28. There are many suitable polarizers such as the plastic polarizing material sold by Polaroid Corporation known as HN7 Linear Polarizer.

Figure 2:
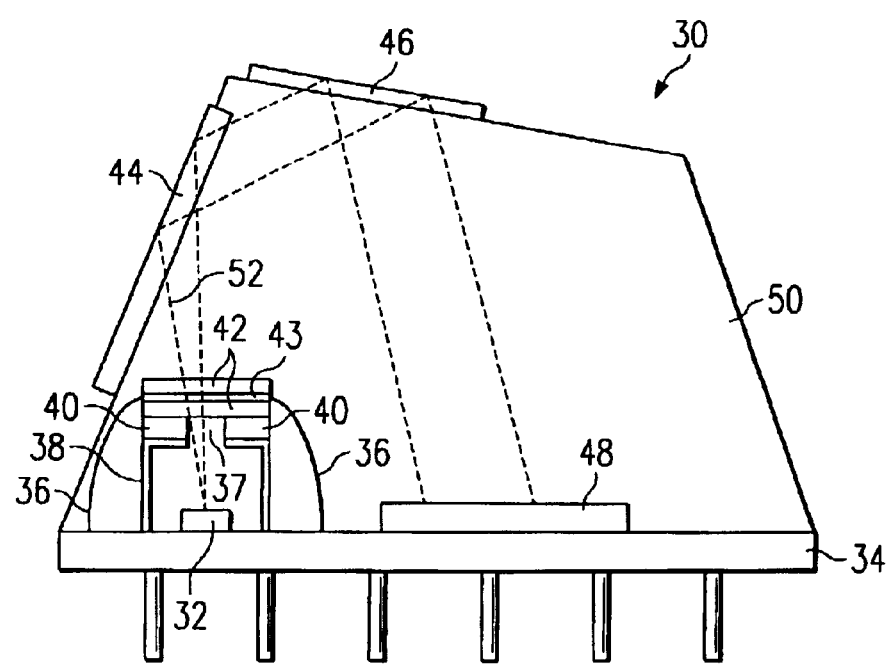
FIG. 2 illustrates an optoelectric biosensor having a liquid crystal switch according to the present invention.

FIG. 2 illustrates an optoelectric biosensor 30 having a liquid crystal switch in accordance with the present invention. In this configuration, sensor 30 is constructed on a substrate 34. A radiation source 32, which may comprise a light emitting diode (LED), a laser diode or any other suitable source of radiation, is disposed internal to a housing 50 and is positioned to direct radiation (light rays) 52 in a direction toward a thin SPR conductive layer 44.

Housing 50 is made of a material which is transparent or substantially transparent to radiation 52 from the electromagnetic radiation source 32. In particular, an epoxy marketed under the trademark Epocast® 2013 Parts A/B by Furane Products Company has been found useful especially for radiation sources in the infrared range. Other usable materials include Emerson & Cumming, Stycast 1269A Parts A/B, Tracon Trabond F114, Dexter Hysol OS1000, Norland 61 and 63,Dexter Hysol MG18 or Nitto 8510-1100.

Radiation source 32 is preferably located above substrate 34 although it can be disposed in substrate 34 itself. A light shield 38 is disposed around the source 32 to prevent stray radiation from being directed throughout the sensor 30. The shield 38 has an aperture 37 which allows radiation from the source 32 to pass therethrough in a generally vertical direction.

A polarizing filter 40 is located near aperture 37 to polarize the light passing through aperture 37 such that the TE component of radiation 52 is transmitted to liquid crystal cell 42, 43 which lies adjacent to polarizing filter 40. Liquid crystal call 42, 43 includes liquid crystal material 43 and a pair of plates 42 wherein plates 42 lie in overlying relation to liquid crystal material 43 such that the liquid crystal material 43 is sandwiched between plates 42. These plates 42 are made of a material which is transparent or substantially transparent to the light from the light source 32. Specifically, liquid crystal material 43 is an organic material which occupies a state of matter in between liquid and solid, where material 43 is fluid but possesses some intermolecular ordering. This organic material is made of anisotropic organic molecules that change orientation upon application of an applied voltage. As is the case, leads 36 connect to material 43 such that a voltage may be applied material 43. When no voltage is applied to material 43, material 43 modulates the transmitted incident radiation 52 having the TE component, such that the molecular direction is made to rotate by 90 degrees through the liquid crystal cell 42, 43 thickness. As a result, transmitted radiation 52 having the TM component emerges from liquid crystal cell 42, 43. When voltage is applied to material 43, material 43 has no effect upon transmitted incident radiation 52 having the TE component, such that radiation 52 having the TE component emerges from liquid crystal cell 42, 43.

In this embodiment, a liquid crystal switch, including polarizing filter 40, liquid crystal material 43, and plates 42, has the ability to effectively switch transmitted light between a first and second state of polarized radiation 52 wherein the first state includes the TM component of the radiation 52 and the second state includes the TE component of the radiation 52.

Accordingly, there are two modes of operation for optoelectric biosensor 30: a first mode whereby no voltage is applied to liquid crystal material 43 to generate a resonance condition for the first state and a second mode whereby voltage is applied to liquid crystal material 43 to generate a non-resonance condition for the second state.

Figure 3A:
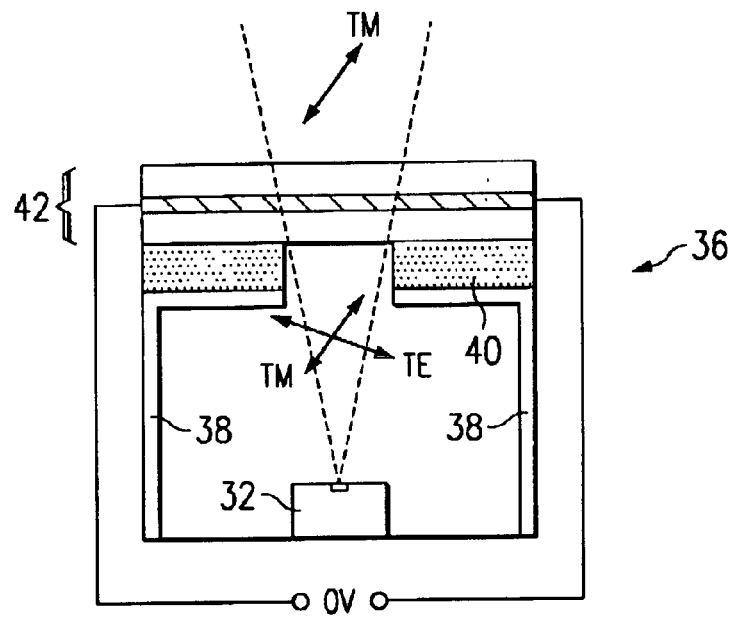
FIGS. 3a and 3b display an electromagnetic radiation path through the liquid crystal switch implemented in the biosensor of FIG. 2 without and with applied voltage, respectively.

In the first mode, when no electric field is applied to liquid crystal material 43, as shown in FIG. 3a, the liquid crystal material 43 modulates the transmitted incident radiation 52 having the TE component, whereby, the molecular direction is made to rotate by 90 degrees through the liquid crystal cell 42, 43 thickness such that radiation 52 having the TM component emerges. Noting that the TM component of radiation 52 is responsive to resonance, thereby generating the resonance condition within sensor 30.

Figure 3B:
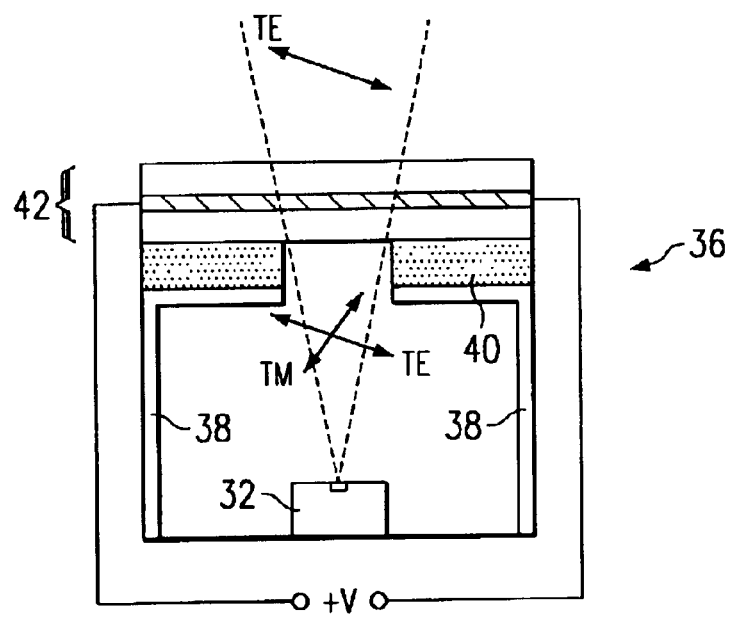

As previously explained, in an effort to reduce time dependent interference, a reference signal is obtained while the dielectric conditions adjacent to the thin SPR conductive metal surface foster an environment where no resonance occurs. Thus, in the second mode, as an electric field is applied to the liquid crystal material 43, shown in FIG. 3b, the molecular axes align with the field and the structure no longer twists the polarization of the incident radiation 52. so the emerging radiation 52, includes the TM component, solely.

Transmitted incident radiation 52 is directed towards a surface plasmon resonance (SPR) layer 44 which is formed on an exterior surface of the optical housing 50. Surface plasmon resonance layer 44 may comprise a thin layer of a conductive material such as copper, silver, gold or aluminum having a substantially uniform thickness. Layer 44 is preferably planar although other configurations, such as convex or concave configurations, or featured with steps, periodic or non-periodic, can also be utilized. This layer 44, in one embodiment of the invention, may comprise a film of gold approximately 275 angstroms thick. The thickness of surface plasmon resonance layer 44 may vary from about 200 to about 600 angstroms and still permit surface plasmon resonance to occur. The specific film thickness is determined by experimentation with respect to the frequency of the radiation for the source 32 and the properties of the conductive material used for layer 44.

As is known in the art, when radiation 52 strikes a thin conductive film 44 at the interface of an insulator, the intensity of reflection therefrom is a function of the angle of incidence of the radiation onto the film 44 and the refractive index of the material in contact with the other side of the film 44. Hence, by determining the angle at which minimum reflectance occurs, it is possible to determine the index of refraction of the material on the side of the film opposite the side the radiation is reflected from.

In accordance with utilizing the principal of operation described above, polarized radiation 52 which is reflected from the thin surface plasmon resonance layer 44 and is directed toward planar mirror 46. Radiation 52, after being reflected from mirror 46 strikes detector array 48. For optical radiation, detector array 48 may comprise an array of photodetectors. Each detector in the array 48 produces a signal on an output pin with an electrical signal that is proportional to the intensity of the radiation striking the detector. By measuring the voltage at each diode of array 48 and knowing the angle that the radiation striking the array 48 intercepted the surface plasmon resonance layer 44, a plot of reflected radiation intensity as a function of the angle may be obtained. This plot correlates to the index of refraction of the substance on the side of the surface plasmon resonance layer 44 opposite the side which reflects the radiation. Accordingly, the signals obtained by array 48 during resonance, when voltage is not applied to liquid crystal material 43, is divided by the reference signal obtained when voltage is applied to material 43 in order to generate the corrected SPR signal reading.

Those of skill in the art will recognize that the physical location of the elements illustrated in FIG. 2 can be moved or relocated while retaining the function described above. For example, the location and shape of the mirrors 46 utilized for reflecting the radiation 52 could take on other configurations and locations so long as radiation 52 strikes a surface plasmon resonance layer 44 and the intensity of the radiation 52 reflected therefrom is measured as a function of the angle of the radiation striking the surface plasmon resonance layer 44. In addition, the location of radiation source 32 can be disposed external to housing 50 and positioned to direct radiation 52 in a direction toward housing 50, so long as housing 50 is shaped to accommodate an optical path that supports surface plasmon resonance.

Furthermore, the liquid crystal switch including plates 42, liquid material 43 and polarizer 22 do not need to be located closely adjacent the aperture 37 but may be disposed at any point along the path of radiation 52 between the source 32 and the detector array 48. There are many suitable polarizers such as the plastic polarizing material sold by Polaroid Corporation known as HN7 Linear Polarizer.

This type of optical sensor can be used in the fields of chemical, biochemical, biological or biological analysis, process control, pollution detection and control and other similar areas.

Advantages of this design include but are not limited to an optoelectric biosensor 30 having a high performance, simple, and cost effective design. This design eliminates the need to expose the surface 44 to air, or high index solutions (e.g. glycerol), when recording a reference signal. Thus, the operation of sensor 30 is simplified and the sensor's performance is significantly improved. In particular, the signal/noise ratio improves.

The reader's attention is directed to all papers and documents which are filed concurrently with this specification and which are open to public inspection with this specification, and the contents of all such papers and documents are incorporated herein by reference.

All the features disclosed in this specification (including any accompany claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

We claim:

1. A surface plasmon sensor comprising:

a source of electromagnetic radiation, the electromagnetic radiation having a transverse magnetic component and a transverse electric component;

a shield, having an aperture, coupled to receive the electromagnetic radiation to minimize the deviation of the direction of the transmitted electromagnetic radiation from the source;

an optical housing, made of material which is capable of transmitting radiation from the source;

a film of conductive material capable for sustaining surface plasmon resonance, the film being disposed on an exterior surface of the optical housing, the optical housing and the film being shaped and positioned so that radiation from the source is reflected by the film;

a sensor array coupled to receive the reflected radiation, the sensor array, sensitive to the reflected radiation, disposed closely adjacent the surface of the housing; and;

a switch disposed between the source and the sensor array to switch between the transverse magnetic component and the transverse electric component of optical radiation such that only one component strikes the sensor array, wherein the transverse electric component of the electromagnetic radiation is utilized to detect optical defects in the surface plasmon sensor.

2. A surface plasmon sensor as recited in claim 1, wherein the switch comprises:

a polarizer to polarize the electromagnetic radiation;

a pair of plates aligned with the polarizer coupled to receive the polarized radiation;

a liquid crystal material coupled between the pair of plates to rotate the molecular direction of the transmitted polarized electromagnetic radiation by 90 degrees such that the switch provides the transverse electric component of optical radiation; and a pair of electrodes, each coupled to a respective opposing end of the liquid crystal material, such that when voltage is applied across the pair of electrodes, the switch provides the transverse magnetic component of optical radiation and cancels the effect of the liquid crystal material on the polarized electromagnetic radiation.

3. A surface plasmon sensor as recited in claim 1, wherein the switch is an electro-optical liquid crystal system.

4. A surface plasmon sensor as recited in claim 1, wherein the sensor array is an array of photodetectors.

5. A surface plasmon sensor as recited in claim 1, wherein the film is a conductive material selected from the group consisting of copper, gold, silver and aluminum.

6. A surface plasmon sensor as recited in claim 1, wherein the source of electromagnetic radiation and the sensor array are mounted upon a common substrate.

7. A surface plasmon sensor as recited in claim 1, further comprising:

at least one optically reflective surface disposed on an exterior surface of the optical housing:

the optically reflective surface, the film and the optical housing being shaped and positioned relative to the source and sensor array such that radiation from the source is reflected by the film and the optically reflective surface and detected by the sensor array.

8. A surface plasmon sensor as recited in claim 7, wherein the optically reflective surface is formed on a curved surface.

9. A surface plasmon sensor as recited in claim 1, wherein the surface of the optical housing on which the surface plasmon resonance layer is formed is a curved surface.

10. A surface plasmon sensor as recited in claim 1, wherein the rays of the radiation striking the surface plasmon resonance layer are diverging from each other.

11. A surface plasmon sensor as recited in claim 1, wherein the rays of the radiation striking the surface plasmon resonance layer are converging toward each other.

12. A surface plasmon sensor as recited in claim 1, wherein the rays of the radiation striking the surface plasmon resonance layer are substantially parallel to each other.

* * * * *